(12) United States Patent
Anand et al.

(10) Patent No.: US 9,758,739 B2
(45) Date of Patent: *Sep. 12, 2017

(54) MOS$_2$ CATALYST SYSTEM FOR THE CONVERSION OF SUGAR ALCOHOL TO HYDROCARBONS

(71) Applicant: PHILLIPS 66 COMPANY, Houston, TX (US)

(72) Inventors: Madhu Anand, Bartlesville, OK (US); Jianhua Yao, Bartlesville, OK (US); Edward L. Sughrue, Bartlesville, OK (US)

(73) Assignee: PHILLIPS 66 COMPANY, Houston, TX (US)

( * ) Notice: Subject to any disclaimer, the term of this patent is extended or adjusted under 35 U.S.C. 154(b) by 19 days.

This patent is subject to a terminal disclaimer.

(21) Appl. No.: 14/168,635

(22) Filed: Jan. 30, 2014

(65) Prior Publication Data

US 2014/0147344 A1    May 29, 2014

Related U.S. Application Data

(62) Division of application No. 13/233,256, filed on Sep. 15, 2011, now Pat. No. 8,673,805.

(60) Provisional application No. 61/444,004, filed on Feb. 7, 2011.

(51) Int. Cl.
| | |
|---|---|
| *B01J 27/051* | (2006.01) |
| *B01J 37/00* | (2006.01) |
| *C01G 39/06* | (2006.01) |
| *C10L 3/08* | (2006.01) |
| *B01J 21/06* | (2006.01) |
| *B01J 37/03* | (2006.01) |
| *C10L 1/04* | (2006.01) |
| *C10G 3/00* | (2006.01) |
| *C07C 1/22* | (2006.01) |

(52) U.S. Cl.
CPC .............. *C10L 3/08* (2013.01); *B01J 21/06* (2013.01); *B01J 27/051* (2013.01); *B01J 37/033* (2013.01); *C07C 1/22* (2013.01); *C10G 3/44* (2013.01); *C10G 3/50* (2013.01); *C10L 1/04* (2013.01); *C10G 2300/1014* (2013.01); *Y02P 30/20* (2015.11)

(58) Field of Classification Search
CPC .......... B01J 27/051; B01J 37/00; B01J 27/06; C01G 39/06
USPC ......................................... 422/187; 502/220
See application file for complete search history.

(56) References Cited

U.S. PATENT DOCUMENTS

| | | | | |
|---|---|---|---|---|
| 4,199,327 A | * | 4/1980 | Hempill et al. | 48/202 |
| 4,243,554 A | * | 1/1981 | Naumann et al. | 502/220 |
| 4,483,691 A | * | 11/1984 | McShea et al. | 48/202 |

(Continued)

FOREIGN PATENT DOCUMENTS

EP          0107358 A2 *  9/1983  ............... B01J 27/02

*Primary Examiner* — Walter D Griffin
*Assistant Examiner* — Huy-Tram Nguyen
(74) *Attorney, Agent, or Firm* — Phillips 66 Company

(57) ABSTRACT

Cellulose and hemicellulose from biomass can be broken down to C6 and C5 sugars and further converted to corresponding sugar alcohols. It is now found that a new catalyst, MoS2, is active for the hydrogenation of sugar alcohols to hydrocarbons. Combining the technologies listed above allows us to convert the cellulose/hemicellulose to liquid hydrocarbons.

3 Claims, 7 Drawing Sheets

(56) References Cited

U.S. PATENT DOCUMENTS

| | | | | |
|---|---|---|---|---|
| 4,853,359 A | * | 8/1989 | Morrison et al. | 502/220 |
| 5,780,381 A | * | 7/1998 | Wilson et al. | 502/308 |
| 8,673,805 B2 | * | 3/2014 | Anand | B01J 21/06 |
| | | | | 502/216 |
| 2001/0051588 A1 | * | 12/2001 | Herron | B01J 23/8896 |
| | | | | 502/302 |
| 2009/0326285 A1 | * | 12/2009 | Bauer | C10G 45/04 |
| | | | | 585/240 |

* cited by examiner

FIG. 5
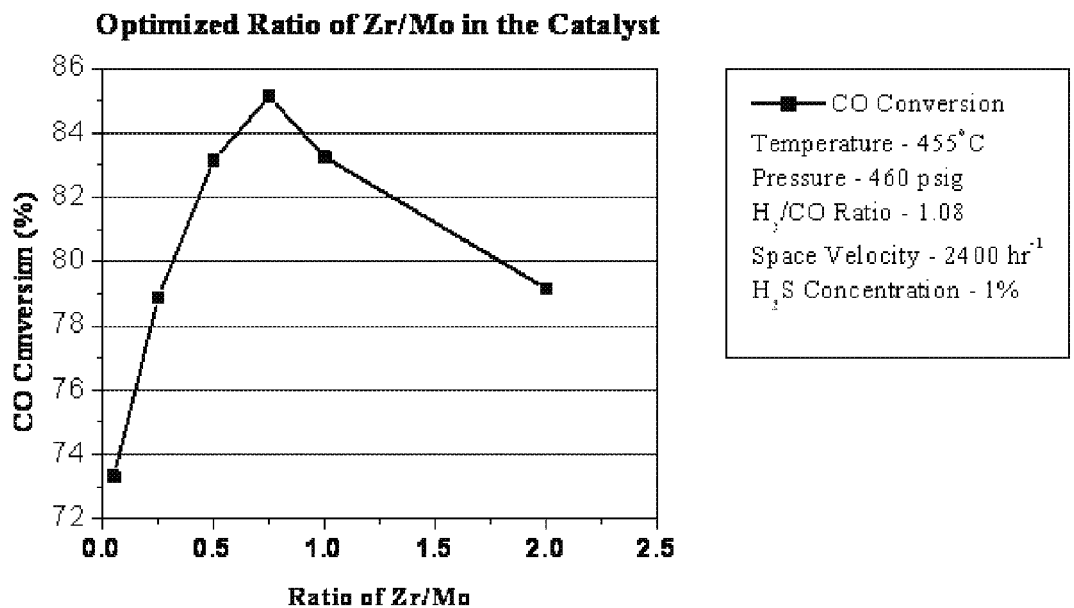
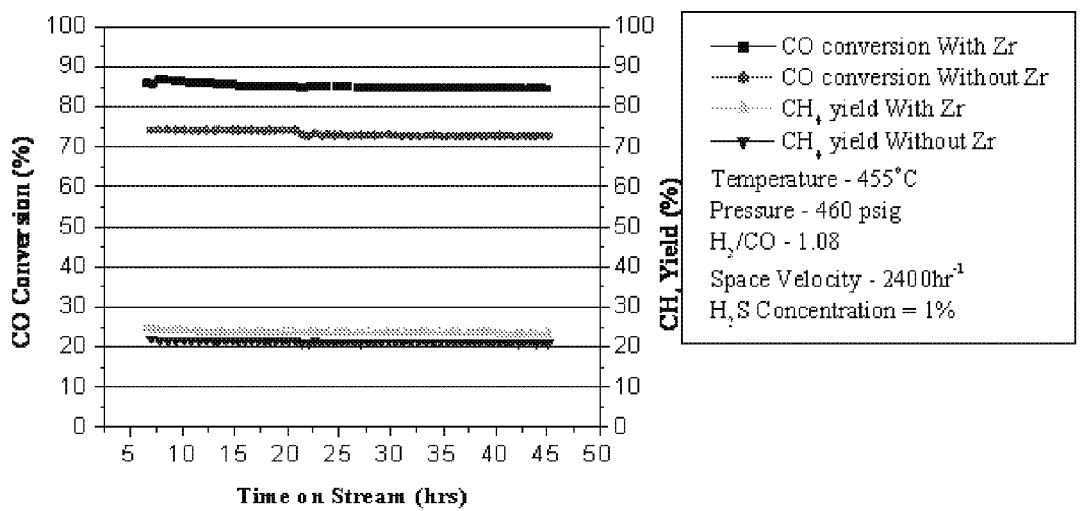
FIG. 6

MoS₂ CATALYST SYSTEM FOR THE CONVERSION OF SUGAR ALCOHOL TO HYDROCARBONS

CROSS REFERENCE TO RELATED APPLICATIONS

This is a divisional application that claims benefit under 35 USC §120 to non-provisional U.S. application Ser. No. 13/233,256 filed Sep. 15, 2011, now U.S. Pat. No. 8,673,805, titled "$MoS_2$ CATALYST FOR THE CONVERSION OF SUGAR ALCOHOL TO HYDROCARBONS," and claims benefit under 35 USC §119(e) to U.S. Provisional Application Ser. No. 61/444,004 filed Feb. 17, 2011, entitled "$MoS_2$ CATALYST FOR THE CONVERSION OF SUGAR ALCOHOL TO HYDROCARBONS," both of which are incorporated herein in their entirety.

STATEMENT OF FEDERALLY SPONSORED RESEARCH

None.

FIELD OF THE DISCLOSURE

The present invention relates generally to catalysts that convert carbohydrates to fuel range hydrocarbons.

BACKGROUND OF THE DISCLOSURE

Methanation is an important process for upgrading coal and biological materials to useful fuel gases. In coal gasification, methanation is the catalytic conversion of hydrogen and carbon monoxide to methane. Methanation is also used to produce biomethane from organic sources of energy. One method of distributing vast quantities of coal and biomass energy is to gasify the coal to produce synthesis gas (syngas) and then convert the syngas to substitute natural gas (SNG) via methanation (Reid, 1973). Current methanation processes use a nickel (Ni) catalyst which imposes certain operating limitations (FIG. 1) because of its susceptibility to deactivation by surface carbon, high temperature requirements, and poisoning by various sulfur compounds. The stringent process restrictions shown in FIG. 1 require additional steps for successful use of nickel catalysts (Walston, 2007).

A major restriction for nickel catalysts comes from their extreme sensitivity to poisoning by sulfur compounds which are always present in coal-derived synthesis gas. Syngas processed by nickel catalysts must be purified to below 20 ppb sulfur to avoid poisoning of the catalyst even though pipeline natural gas can contain up to 4 ppm hydrogen sulfide. Nickel catalysts can also be irreversibly poisoned by carbon fouling. To avoid carbon fouling the $H_2/CO$ ratio has to be adjusted to values greater than three by the water-gas-shift (WGS) reaction. Nickel catalysts are also deactivated by sintering at high temperatures (>450° C.). The methanation reaction is so highly exothermic that a 5 mole percentage reduction in carbon monoxide (CO) concentration due to the methanation reaction results in about a 260° C. (500° F.) increase in reactor temperature. Ni catalysts are so active that it is hard to obtain less than 100% CO conversion even at high space velocities. Therefore, in industrial plants, around 90% of the product gas from the methanation reactor is recycled back to dilute the concentration of CO to less than 5% (mol) in the feed gas. Lurgi designed the Great Plains Synfuels Plant in North Dakota using this conventional methanation technology (Lukes, 2003; Anand, 2007). This is the only existing example of a commercial coal to SNG facility and has been operating since July 1984.

Improvements to the conventional methanation process were made by Haldor Topsoe and Johnson Matthey by developing a high temperature methanation technology. Haldor Topsoe developed a Ni-based, thermally stable methanation catalyst, MCR-2X, for a high temperature methanation process, trade marked as TREMP™ (Total REcycle Methanation Process) (Udengaard, 2006). This catalyst can be operated at higher temperatures than previous Ni catalysts and does not sinter below 700° C. (~1250° F.). The methanation unit is made up of a series of adiabatic methanators with inter-stage cooling and gas recycle to control the reactor temperature. As a result of the higher temperature tolerance of the catalyst, per pass CO conversion can be increased. This allows for smaller recycle ratio and methanation reactor size resulting in lower CapEX and OpEX than conventional methanation. The higher effluent gas temperature at the reactor outlet can be used to generate superheated, high pressure steam to further improve energy efficiency of the process. This process was demonstrated in a single 1.7 mmscf/d reactor in the 1980's.

Johnson Matthey has developed a similar high temperature methanation technology. Their catalyst is a modified version of their Ni-based pre-reformer catalyst traditionally used in hydrogen and/or ammonia plants. A newer generation of high temperature methanation catalyst, CRG-LH, was formulated in the 1990's, for improved thermal stability. According to Johnson Matthey, this catalyst has been tested on a pilot scale reactor (¾" diameter, 8 ft long) at 500-600° C. (~1100° F.), 30-50 bar for over 1000 hours. The results showed acceptable thermal stability. Demonstration of this catalyst on a larger reactor seems necessary to fully evaluate its commercial capability.

Other improvements to the conventional methanation process are combined shift/Methanation (Graboski, 1975), sulfur-tolerant methanation and catalytic steam gasification. Combined shift/methanation technologies such as Conoco's SUPER-METH™ (Kock, 1979; Sudbury, 1980) Parson's RMPROCESS™ (Dissinger, 1980; White, 1975; White, 1976), United Catalyst, ICI, and UOP utilize water formed in methanation for water-gas-shift and hence combine the water-gas-shift and methanation reactions into a single reactor. Apart from an acid gas removal unit upstream of the methanation reactor for $H_2S$ removal, an additional acid gas removal unit is required downstream of the shift/methanation process to remove CO2. These technologies were piloted in the 1970s but have not proven to be commercially viable due to costs, complexity, scalability or other complications associated with the demands of refinery methanation processes.

The sulfur-tolerant methanation process developed by the Gas Research Institute (GRI) (U.S. Pat. No. 4,491,639; EP0120590; Happel, 1979; Happel, 1981; Happel, 1982; Happel, 1983; Happel, 1985; Happel, 1980; Huang, 1990; Lee, 1987) in the 1970s is shown in FIG. 1. It shows significant improvements over the conventional methanation and combined shift/methanation processes. The sulfur-tolerant methanation process developed by the Gas Research Institute (GRI) uses a molybdenum based ($MoS_2$) sulfur-tolerant catalyst (Happel, 1982). According to the GRI study, the process shows potential savings in steam usage, reduced recycle rate and a smaller acid gas removal unit. This process was piloted extensively by GRI from 1978 to 1985 in an adiabatic reactor system. The reactor was made from 1" Schedule 80 pipe loaded 4" deep with ⅛" cylindrical catalyst pellets. Their GRI-C-525 catalyst ran for 10,000 hours and the GRI-C-600 catalyst ran for 2,300 hours.

When a nickel (Ni) catalyst is used for methanation and Ni catalyst is susceptible to coke formation, sulfur poisoning, and sintering. To solve these problems, a couple of unit operations such as water-gas-shift (WGS) and acid gas removal (AGR) are required before the methanation reactor. Synthesis gas from the gasifier goes through a sulfur-tolerant WGS reactor to adjust the $H_2/CO$ ratio to 3:1 (Reaction 1). Then, CO2 and sulfur compounds are removed from the hydrogen rich synthesis gas in an AGR unit before supplying it to a methanation reactor (Reaction 2).

Water-Gas-Shift Reaction:

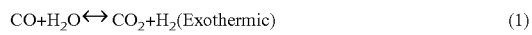

$$CO + H_2O \leftrightarrow CO_2 + H_2 (\text{Exothermic}) \quad (1)$$

Methanation Reaction:

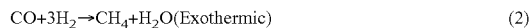

$$CO + 3H_2 \rightarrow CH_4 + H_2O (\text{Exothermic}) \quad (2)$$

Catalytic steam gasification is another methanation technology, which was first piloted by Exxon (Nahas, 1983; Nahas, 2003; Nahas, 2004; Nahas, 1978; Nahas, 1978) in the 1970s (Anand, 2008). Recently, GreatPoint Energy (GPE), a new technology company, has done pilot plant campaigns in a 1.5 ft reactor on catalytic steam gasification and has plans to build a pilot facility in Somerset, Mass. Although it eliminates the need for an air separation plant, reduces the size of the acid gas removal unit and also combines gasification, shift and methanation reactions into a single reactor, many operational issues must be proven in the Somerset pilot runs to determine if this process is economical.

One possible alternative source of hydrocarbons for producing fuels and chemicals is the natural carbon found in plants and animals, such as for example, in the form of carbohydrates. These so-called "natural" carbon resources (or renewable hydrocarbons) are widely available, and remain a target alternative source for the production of hydrocarbons. For example, it is known that carbohydrates and other sugar-based feedstocks can be used to produce ethanol, which has been used in gasohol and other energy applications. However, the use of ethanol in transportation fuels has not proven to be cost effective and may not be achievable on a scale significant to current fuel requirements.

Carbohydrates, however, can also be used to produce fuel range hydrocarbons. Although some upgrading technology has been developed to turn biologically derived materials into useful fuel and chemical feedstocks. Unfortunately, many carbohydrates (e.g., starches) are undesirable as feedstocks due to the costs associated with converting them to a usable form. In addition, many carbohydrates are known to be "difficult" to convert due to their chemical structure, the hydrocarbon product produced is undesirable, or the conversion process results in relatively low yields of desirable products. Among the compounds that are difficult to convert include compounds with low effective hydrogen to carbon ratios, including carbohydrates such as starches, sugars, carboxylic acids and anhydrides, lower glycols, glycerin and other polyols and short chain aldehydes.

Cortright et al. US2008/0216391 teaches processes and reactor systems provided for the conversion of oxygenated hydrocarbons to hydrocarbons, ketones and alcohols useful as liquid fuels, such as gasoline, jet fuel or diesel fuel, and industrial chemicals. Abhari, US2009/0054701A1 relates to a process for converting by products of the manufacture of biodiesel into industrially useful oxygenated products of greater commercial value.

Molybdenum disulfide ($MoS_2$) based catalysts are important industrial catalysts used in the removal of sulfur compounds from crude petroleum by hydrogenolysis. from Chemical Engineering nanostructured crystals of $MoS_2$ (CE, April p. 15), a highly porous form of $MoS_2$ has also been produced by researchers at the University of Illinois at Urbana-Champaign (edlinks.che.com/4819-541). In U.S. Pat. No. 7,435,760, Hertling et al. propose using an alkali doped Cu catalyst, $MoS_2$ catalyst, and Rh based catalysts to convert synthesis gas to higher alcohols. Different procedures and catalysts have been developed to get active $MoS_2$ catalytic sites on the surface of the catalyst (Fujikawa, U.S. Pat. No. 7,361,624). Additionally, NiMoS and CoMoS catalysts are commercially available from CENTINEL® and ASCENT® based on surface deposition of flat catalyst active sites, but this method of synthesis is limited to surfaces or platelets of catalyst activity which is not ideal for all $MoS_2$ catalyzed reactions.

As such, development of an improved catalysts for converting carbohydrates, including "difficult" to convert starches as mentioned above, to hydrocarbon, would be a significant contribution to the arts. In addition, development of a process for converting carbohydrates to hydrocarbons which yields significant quantities of desirable hydrocarbon products such as aromatics and olefins would be a significant contribution to the art.

BRIEF DESCRIPTION OF THE DISCLOSURE

In one embodiment, a sulfur-tolerant methanation catalyst was synthesized and a sulfur-tolerant methanation process was developed. A stable sulfur-tolerant methanation will increase catalyst longevity, increase product production and reduce plant operating costs. In one embodiment, an $MoS_2$ catalyst with Zirconium promoter and elemental sulfur unexpectedly improved space velocity, temperature, and $H_2S$ tolerance of the catalyst.

To convert biomass to liquid hydrocarbon fuels, a novel molybdenum disulfide catalyst has been developed that improves the overall number of active $MoS_2$ sites on the surface of the catalyst. Methods of synthesizing the active catalyst and use of the hydrogenation catalyst are described. The ZrMoS hydrogenation catalyst converts C6 and C5 sugars to sugar alcohols on a commercial scale. The ZrMoS catalyst remains active in the presence of sugar alcohols and other products in aqueous biomass conversion process. Sugar alcohols, such as sorbitol, are hydrogenated to C6 hydrocarbons using a newly developed ZrMoS catalyst with a high density of surface active $MoS_2$ catalytic sites.

Molybdenum based sulfur-tolerant catalysts were studied to replace nickel catalysts for the conversion of synthesis gas to substitute natural gas (SNG). Using a zirconium promoter with elemental sulfur during co-precipitation synthesis increased the stability and activity of the catalyst, thus decreasing catalyst cost, increasing productivity and conversion rates. Other promoters and presulfiding conditions were unable to provide these significant improvements. Process conditions such as space velocity, temperature, and $H_2S$ concentration increased activity of the $MoS_2$ catalyst.

A methanation catalyst comprising: molybdenum sulfate (MoS2), zirconia (Zr), and elemental sulfur (Sx), wherein the MoS2 methanation catalyst is co-precipitated in the presence of Zr at a pH of greater than 3.0.

A process for hydrogenation of oxygenates comprising: contacting a Zr/MoS2 methanation catalyst with R—C—O in the presence of hydrogen, and purifying produced hydrocarbons, wherein the MoS2 methanation catalyst is co-precipitated in the presence of Zr at a pH of greater than 3.0.

A substitute natural gas production system comprising: a gasifier unit, an oil quench unit, a water quench and ammonia recovery unit, a methanation unit, wherein the methanation unit comprises an $MoS_2$ methanation catalyst, a $CO_2$ and water removal unit, and a sulfur removal unit, wherein said MoS2 methanation catalyst was co-precipitated in the presence of Zr at a pH of greater than 3.0.

The methanation catalyst may be a co-precipitation of a $MoS_2$ catalyst with Zr at a pH of about 3.0, 3.5, 4.0, 4.5, 5.0, 6.0 or greater. The methanation catalyst can use $NiNO_3$, $MgNO_3$, $K_2CO_3$, $PdNO_3$, Silica, or Alumina as promoters, as well as combinations of these promoters. The catalyst may be presulfided between ~450° C. and ~500° C., with $N_2$, $H_2$, DMDS, and combinations thereof; including but not limited to ~500° C. with $N_2$, $H_2$ and DMDS; ~500° C. with $H_2$ and DMDS; ~500° C. with $N_2$, $H_2$ and $H_2S$; or ~500° C. with $H_2$ and $H_2S$. The catalyst may contain a ratio of Zr/Mo between about 0.6 and about 0.8. Additionally, the catalyst may be synthesized with elemental sulfur.

BRIEF DESCRIPTION OF THE DRAWINGS

A more complete understanding of the present invention and benefits thereof may be acquired by referring to the follow description taken in conjunction with the accompanying drawings in which:

FIG. 5: CO conversion for methanation as a function of ratio of moles of zirconium and molybdenum in order to obtain the optimized ratio for enhanced MoS2 catalyst activity.

FIG. 6: CO conversion and methane yield for sulfur-tolerant MoS2 catalyst with or without zirconia as a promoter for the production of substitute natural gas from synthesis gas.

DETAILED DESCRIPTION OF EMBODIMENTS OF THE INVENTION

Figure 1:
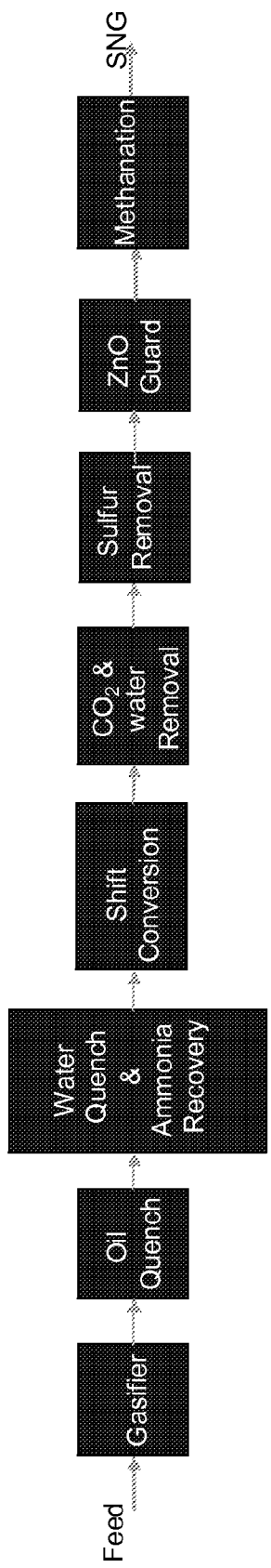
FIG. 1: Unit operations required for the production of substitute natural gas from synthesis gas using a nickel catalyst.
Figure 2:
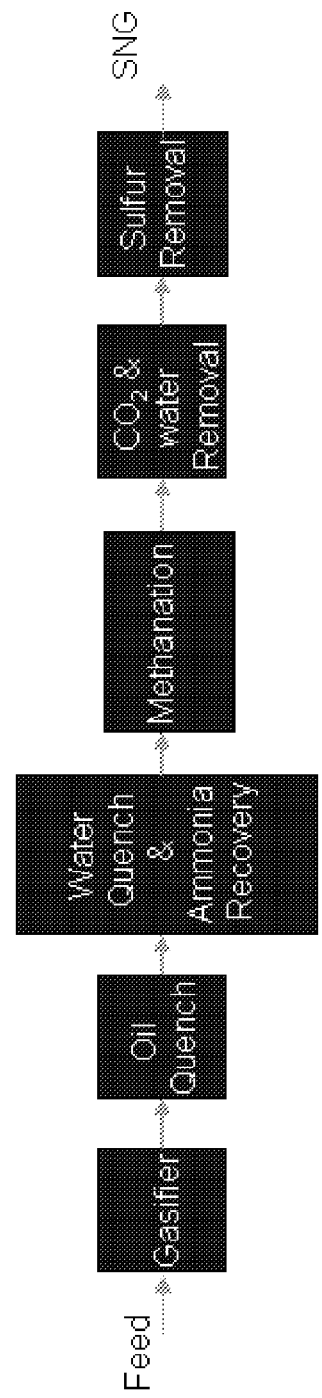
FIG. 2: Unit operations required for the production of substitute natural gas from synthesis gas using a $MoS_2$ catalyst.

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

Cellulose and hemicellulose are two major constituents in the biomass and can be broken down to C6 and C5 sugars using an acid or enzyme hydrolysis process. C6 and C5 sugars can be further converted to sugar alcohols or other derivatives. The sugars and their derivatives can be upgraded to gasoline range hydrocarbons, mainly aromatics, using a ZSM-5 catalyst, hydrotreating or combinations of ZSM-5 and hydrotreating. However, the sugars and sugar derivatives with less effective hydrogen to carbon ratio are easily converted to coke and frequently lower liquid yield, foul expensive refining catalysts and other equipment. Addition of hydrogen donors with high effective hydrogen to carbon ratio such as methanol (US4503278) and i-pentane (U.S. Pat. No. 7,678,950) have been used to decrease coking, incorporated by reference. U.S. Pat. No. 6,090,990 describes an improved catalyst containing a mixture of zeolite and a binder treated with boron trichloride which is then used in the conversion of hydrocarbons to ethylene, propylene and BTX (benzene, toluene, xylene and ethylbenzene) aromatics. U.S. Pat. No. 7,550,634 describes hydrotreating triglycerides to fuel range hydrocarbons. In U.S. Ser. No. 61/236,347, by Sughrue, et al., describes hydrotreating a mixture of sorbitol and diesel over a commercial hydrotreating catalyst to produce lighter alkanes and hexanes desirable for gasoline fuels. Additionally, in U.S. Ser. No. 61/248,099, Yao, et al., describe the process of converting carbohydrates to gasoline boiling range hydrocarbons by converting a carbohydrate-containing material to a hydrogenated carbohydrate material over a bi-functional catalyst and then converting the hydrogenated carbohydrate material to gasoline boiling range hydrocarbons over a zeolite catalyst. In U.S. Ser. No. 61/288,912, Yao, et al., use a zinc-platinum or cobalt-molybdenum impregnated zeolite catalyst (ZnPt-zeolite or CoMo-zeolite) with a carbohydrate or polyol to produce polyols and hydrocarbons. In U.S. Ser. No. 61/424,896, Bares, et al., use a single-step hydrotreating process to convert oxygen-containing hydrocarbons (preferably, biomass-derived hydrocarbons) that allows a lower conversion temperature to be utilized relative to conventional hydrotreating over a CoMo catalyst. These patents and applications referenced above are specifically incorporated by reference in their entirety.

Carbohydrates, such as starches and sugars may be converted in accordance with the present invention to form a hydrocarbon mixture useful for liquid fuels and chemicals. The term, "carbohydrate" is used generally to refer to a compound of carbon, hydrogen and oxygen having the general formula $C_x(H_2O)_y$, in which the ratio of hydrogen to oxygen is the same as in water. Carbohydrates include monosaccharides, polysaccharides, and mixtures of monosaccharides and/or polysaccharides. The term "monosaccharide" or "monosaccharides" are generally hydroxy aldehydes or hydroxy ketones which cannot be hydrolyzed into any simpler carbohydrate. Monosaccharides can be a triose with 3 carbon atoms, tetrose with 4 carbon atoms, pentose with 5 carbon atoms, hexose with 6 carbon atoms, or larger monosaccharides like Sedoheptulose with 7 carbon atoms or Neuraminic acid with 9 carbon atoms. Examples of monosaccharides include glyceraldehyde, erythrose, xylose, dextrose, glucose, fructose and galactose. The term "polysaccharide" or "polysaccharides" include those saccharides containing more than one monosaccharide unit. This term also includes disaccharides (such as sucrose, maltose, cellobiose, and lactose) and oligosaccharides.

Carbohydrate feedstock comprises a mixture of one or more carbohydrate derivatives including polysaccharides, monosaccharides, polyols, sugars and sugar alcohols from a variety of sources, as well as other byproducts of biological degradation that aren't removed as solids or are not completely removed by other processes. In some examples a single polyol, such as sorbitol or xylitol in aqueous solution is used as a carbon feedstock. Sugar feedstocks consist of one or more polyols in an aqueous solution. Polyols include glycerol, sorbitol, xylitol, and the like. Liquefaction of biomass typically produces monoglyceride feedstocks containing sorbitol and xylitol. Feedstocks may contain from about 50 to about 98% v/v polyol. In one embodiment a polyol feedstock contains approximately 30%, 35%, 40%, 45%, 50%, 55%, 60%, 65%, 70%, 75%, 80%, 85%, 90%, 95%, up to 98% sorbitol, xylitol and mixtures of sorbitol and xylitol. Although sorbitol feedstock comprises sorbitol and aqueous solution, additional polyols, oils, and sugars are present after liquefaction. Many isomers, polymers, and soluble sugars are present in the aqueous liquefaction fraction. Examples of carbohydrates useful as starting materials in accordance with the present invention include, but are not limited to, polysaccharides such as sucrose, maltose, lactose, cellobiose, melibiose, raffinose, starch (derived from a variety of cereal grains such as wheat and rice, tubers such as potato, tapioca, and arrowroot, or waxy starches such as waxy maize) and starch decomposition products such as dextrin and corn syrup (also known as glucose syrup).

Sulfur-Tolerant Methanation: Molybdenum catalyst has both WGS and methanation activity. The reaction occurring in the methanation reactor is likely to be a combination of reactions 1 and 2 (above) as shown in reaction 3. This eliminates the need for a WGS reactor.

Methanation Reaction:

$$2CO + 2H_2 \rightarrow CO_2 + CH_4 \text{(Exothermic)} \qquad (3)$$

Apart from being sulfur-tolerant, $MoS_2$ catalyst also methanates the raw syngas directly by using equimolar amounts of carbon monoxide and hydrogen. There is no requirement for a water-gas-shift reactor before the methanation reactor with a $MoS_2$ catalyst, resulting in steam usage savings. Also because the $MoS_2$ catalysts are sulfur-tolerant, sulfur impurities have to be removed to only 4 ppm levels in the product gas (pipeline specification) instead of 20 ppb in the synthesis gas (nickel catalyst specification). In addition, the position of the acid gas removal unit can be changed from upstream of the methanation reactor to downstream of the methanation reactor resulting in a decrease in gaseous moles processed by the acid gas removal unit. This results in potential savings due to the smaller size of acid gas removal unit. Molybdenum catalysts also operate at higher temperature than Ni catalysts resulting in lower catalyst sintering during methanation.

Example 1: Promoter Effects $MoS_2$ catalysts with various promoters were prepared in this study. Catalysts were prepared by co-precipitation using ammonium tetrathiomolybdate as the molybdenum precursor. Catalyst preparation began with the precipitation of amorphous $MoS_3$ along with $ZrO_2$. Various other promoters were also tested along with zirconium. A salt solution was prepared by mixing two aqueous solutions—4 grams of ammonium tetrathiomolybdate in 61.52 mL of water, and 1.776 grams of zirconyl hydrate nitrate in 6 mL of water. Two peristaltic pumps were used to slowly add dilute nitric acid (0.1 M) and the mixed salt solution to a 500 mL beaker filled with 100 mL water. The beaker was vigorously stirred and pH was maintained constant throughout the precipitation process by adjusting the flow rates of the solutions. Precipitation was done at various pH levels to study their impact on the activity of the catalyst. The resulting slurry was filtered and washed with distilled water and acetone. The filtered cake was added to 1.538 grams of sulfur stirred in acetone. The acetone was allowed to evaporate and then the resultant cake was further dried in an oven under $N_2$ atmosphere for 4 hrs at 80° C. (~175° F.). The dried mixture was collected, weighed, pelletized and prepared for presulfiding and reduction for further evaluation.

TABLE 1

CO conversion and methane selectivity for various promoters

| Promoters | CO Conversion (%) | CH$_4$ Selectivity (%) | Deactivation Rate (%/hr) |
| --- | --- | --- | --- |
| MoS$_2$ Catalyst with Zirconia Promoters | 85 | 52 | 0.005 |
| 1% NiNO$_3$ | 76 | 51 | 0.255 |
| 10% NiNO$_3$ | 36 | 46 | 0.256 |
| 10% MgNO$_3$ | 85 | 52 | 0.083 |
| 3.5% K$_2$CO$_3$ | 83 | 52 | 0.008 |
| 1% PdNO3 | 67 | 51 | 0.471 |
| 1% Silica | 80 | 52 | 0.026 |
| 1% Alumina | 80 | 52 | 0.013 |

Other promoters such as Ni, Pd, Mg, K, Al, Si, and Ti were added at 1% by catalyst weight with or without zirconium during co-precipitation. Catalytic materials were characterized by Analytical Services using x-ray fluorescence (XRF), nitrogen physisorption (BET) and x-ray diffraction (XRD) to determine elemental content, BET surface area and crystal structure.

To evaluate the catalyst activity, 3.8 mL of $MoS_2$ catalyst mixed with 6.2 mL of alundum was loaded into a ½ inch stainless steel reactor to produce a 10 mL catalyst bed. The catalyst was pre-sulfided by rapidly heating the reactor at 460 psig with $N_2$ flowing at a rate of 45 sccm along with 3% $H_2S$. $H_2S$ can be provided either directly as $H_2S$ gas or by the thermal decomposition of dimethyl disulfide liquid (DMDS). The reactor was heated to about 500° C. (~930° F.) in less than 15 minutes to have fast reduction and to obtain a high surface area $MoS_2$ catalyst. After achieving 450° C. (~840° F.), the nitrogen gas flow was switched to a stream of hydrogen (45.5 sccm) along with DMDS flow at 0.15 mL/hr. The catalyst was held under $H_2$ and DMDS flow at 500° C. for 5 hrs to fully reduce the $MoS_3$ phase to the $MoS_2$ phase. After 5 hours, the catalyst was evaluated using reaction conditions.

DMDS feed as a $H_2S$ source was pumped to the system using an ISCO Model 500 D syringe pump while gases were supplied by Brooks 5850E mass flow controllers. The temperature at the center of the catalyst bed was measured using a type K thermocouple inside a thermowell in the reactor. Pressure was maintained using a Tescom back pressure regulator. Analysis of the reactor effluent was completed using an online Agilent 6890 gas chromatograph outfitted with a 15'×⅛" stainless steel 60/80 mesh size carboxen-1000 column (0.5 g/ft packing density) plumbed to a thermal conductivity detector. Periodically a gas bomb was used to collect the reactor outlet, which was analyzed either by detailed hydrocarbon analysis or by mass spectroscopy.

A series of $MoS_2$ catalysts were prepared at various pH levels by co-precipitation to study the effect of elemental sulfur, types and composition of various promoters, presulfiding chemical and presulfiding temperature. These catalysts were evaluated at a feed composition (mol) of 34% CO, 37% $H_2$ and 28% $N_2$. A $H_2$/CO mole ratio of 1.08 was picked for molybdenum catalysts because the E-Gas gasifier can provide this ratio with some types of coals by putting some extra steam in the second stage of gasifier. A space velocity of 2400 $hr^{-1}$ was used because it is close to the fresh feed space velocity for conventional methanation (Ni catalyst) in industrial plants, which is around 2000 $hr^{-1}$. Catalysts were evaluated at various percentages of $H_2S$, space velocities, and reaction temperatures.

For the activity test, unless otherwise stated, reactor pressure was 460 psi with a gas hourly space velocity (GHSV) of 2400 $hr^{-1}$ and hydrogen to CO ratio ($H_2$/CO) of 1.08. Furnace temperature was set at 455° C. (~850° F.). The syngas feed stream was 37% $H_2$, 34% CO, 1% $H_2S$ and the remaining inerts in the syngas were substituted with $N_2$ flow at 28%. These reaction conditions were chosen to compare the catalyst activity with the GRI catalyst.

Example 2: Catalyst Synthesis Parameters

Figure 3:
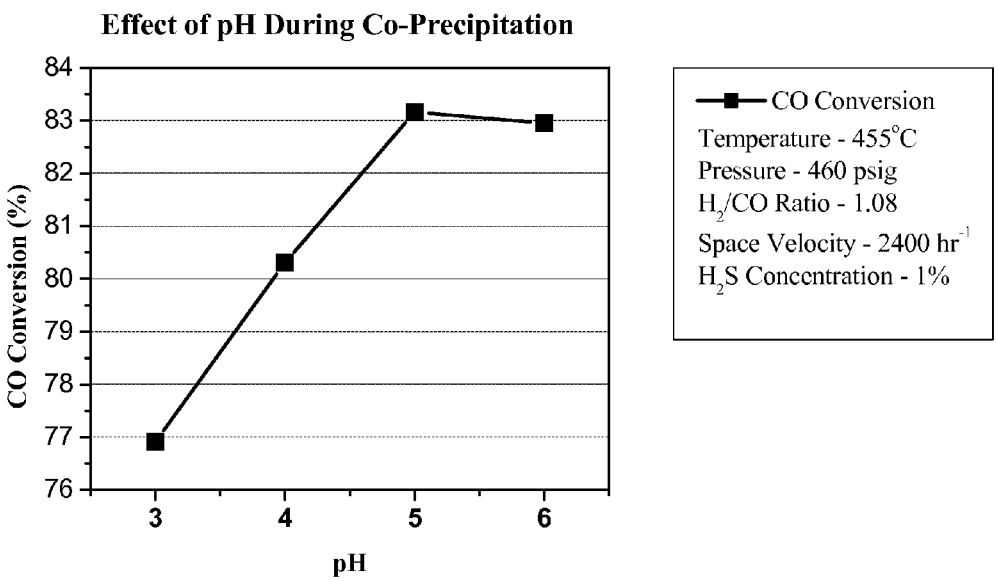
FIG. 3: CO conversion for methanation using $MoS_2$ catalysts prepared at different pH levels during co-precipitation. Constant pH levels were obtained by controlling the flow rates of the two peristaltic pumps for the mixed salt solution and the 0.1M nitric acid solution.
Figure 4:
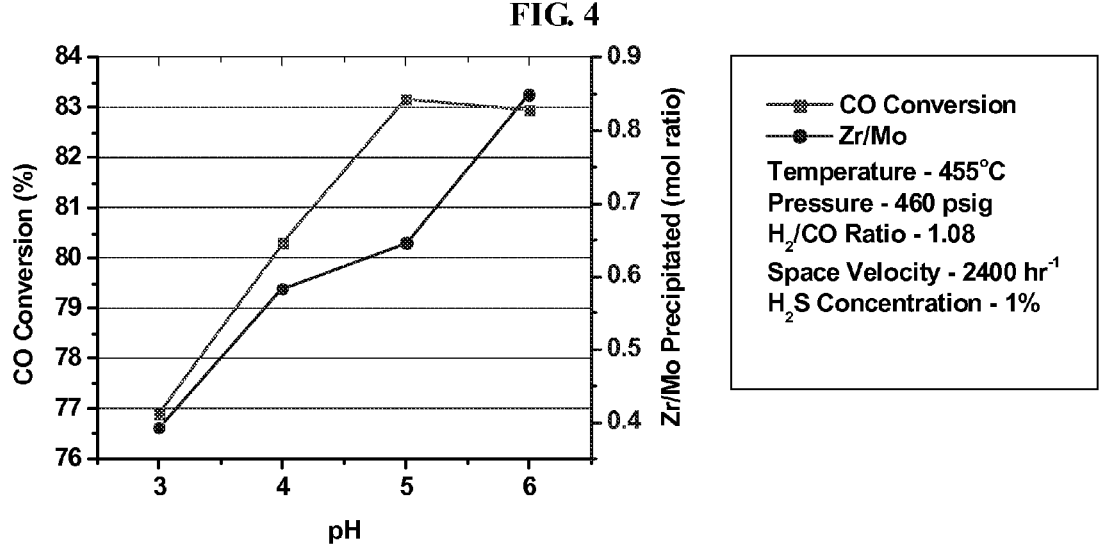
FIG. 4: CO conversion and Zr/Mo ratio precipitated as a function of pH levels during co-precipitation.

Effect of pH during Precipitation: In this work, a constant pH of 3, 4, 5, or 6 was maintained during catalyst synthesis. The constant pH was obtained by using two peristaltic pumps set at appropriate flow rates to mix the salt solution with the nitric acid solution (0.1M). Catalysts obtained were evaluated and compared for CO conversion and methane selectivity. Selectivity of methane was almost the same for all the catalysts prepared. The effect of pH on CO conversion is shown in FIG. 3. It is clear that the catalyst precipitated at pH 5 gives the maximum conversion. After analyzing the catalyst samples with PVSA (pore volume surface area), Karnak and XRD studies, it was observed that the effect of pH on CO conversion is not due to the presence of different catalyst phases or surface areas but due to the ratio of Zr to Mo precipitated in the catalyst synthesis. As shown in FIG. 4, the Zr/Mo ratio (mol) precipitated during catalyst preparation follows a trend with the pH of the solution. Near pH 5 an optimized ratio of Zr to Mo was precipitated compared to ratios precipitated at other pH levels. The optimum ratio of Zr/Mo lies between 0.6 and 0.8. Because it is hard to make very small changes in the pH in order to find exact optimum Zr/Mo ratio, experiments were run to find out the optimum ratio of zirconium to molybdenum in the bulk salt solution.

Example 3: Zirconium Promoter

Experiments were run to find out the optimum amount of zirconium in the bulk salt solution for the given amount of molybdenum for the improved activity. It can be noticed from the plot (FIG. 5) between CO conversion and the ratio of moles of Zr to Mo, that there is a maximum in the CO conversion at a ratio of 0.75 moles of zirconium to molybdenum. Up to a ratio of 0.75, there is an increase in the CO conversion and it decreases with the further increase in zirconium amount. FIG. 6 shows the CO conversion and methane yield data for $MoS_2$ catalysts with and without zirconia as a promoter. It is clear from these data that zirconia enhanced the catalyst activity without changing the stability of the catalyst under the given conditions. Zirconia improved the CO conversion from 73% to 85% and methane yield on the basis of weight from 21.3% to 23.7%.

The basic structure of the catalyst can be varied by the incorporation of additional elements such as nickel, magnesium, potassium, palladium, aluminum, silicon, or titanium as promoters (Cover, 1989). In this study, catalysts were synthesized with these elements at 1-10 wt % of the catalyst. As shown in the Table 1, CO conversion and methane selectivity did not show any improvement compared to $MoS_2$ catalyst with 0.75 moles of zirconium to molybdenum. There was also not much influence on the stability of the catalyst as it is shown from the deactivation rate. Deactivation rate is given in terms of loss in percentage of CO conversion per day.

Example 4: Elemental Sulfur

Figure 7:
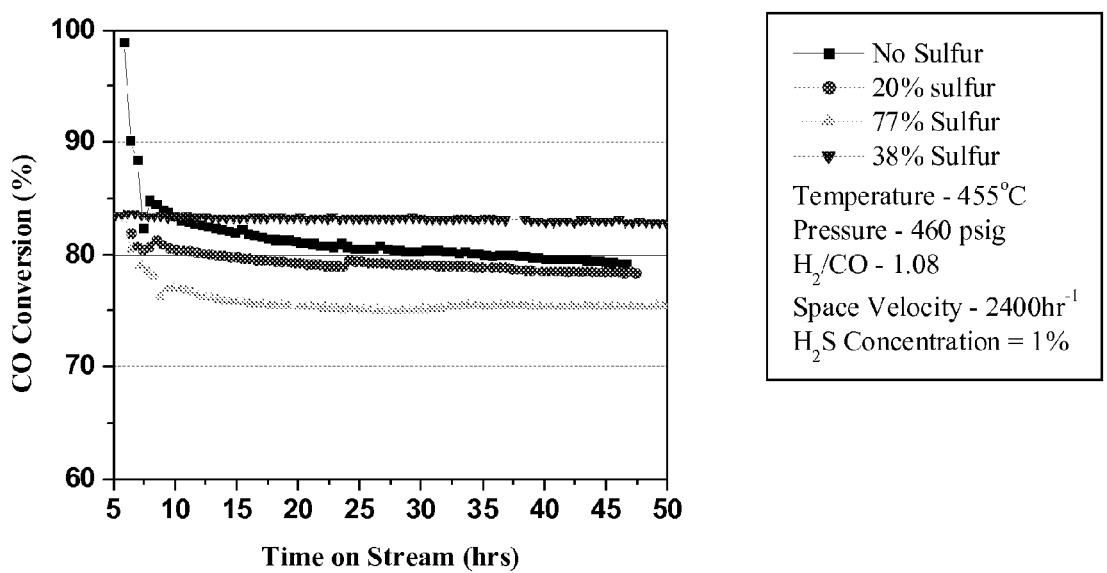
FIG. 7: CO conversion for sulfur-tolerant MoS2 catalyst with or without addition of elemental sulfur during the catalyst synthesis. Various multiples of the optimized amount of elemental sulfur (38 wt % of the catalyst) were evaluated.

It was discovered that addition of elemental sulfur during the co-precipitation of the $MoS_2$ catalyst, followed by its removal as $H_2S$ by reduction, improves catalytic stability and activity. $MoS_2$ catalysts were synthesized with and without elemental sulfur and analyzed for methanation activity. It is clear from FIG. 7 that sulfur is important for stability and its quantity has a small effect on the catalyst activity. The black curve is shown for CO conversion for a catalyst without sulfur. There is decline over time in the CO conversion from 84% to 79% as seen from 45 hours of data for the $MoS_2$ catalyst synthesized without sulfur. On the other hand, the dark curve shown for the optimized amount of sulfur (38 wt % of the catalyst) is stable and CO conversion is constant at 84% for 45 hours. CO conversion for the red curve, shown for half the optimized amount (20 wt % of the catalyst), also declines from 81% to 79%. Alternatively, the green curve, shown for double the amount of optimized sulfur (77 wt % of the catalyst), is fairly stable but CO conversion is around 76%.

Example 5: Presulfiding Conditions

Effect of Presulfiding Temperature: The surface area of molybdenum disulfide depends strongly on the rate of conversion of molybdenum trisulfide to disulfide. Rapid conversion of trisulfide to disulfide at 450° C. either by reduction with hydrogen or thermal decomposition results in molybdenum disulfide of unusually high surface area: 135-155 m2/gm. On the other hand, slow conversion gives surface areas as low as 2 m2/gm. There is an optimum temperature around 450° C. for carrying out reduction. This optimum temperature is due to competition between the rate of nucleation of $MoS_2$ and rate of sintering of $MoS_2$ crystals after formation. A number of experiments were conducted to evaluate different reduction temperatures around 450° C. and results are given in Table 2. Since the CO conversion was decreasing with temperature, the $MoS_2$ catalyst was not tested below 450° C.

TABLE 2

Comparison of CO conversion and methane Selectivity for various presulfiding temperatures and presulfiding media evaluated during MoS2 catalyst reduction and presulfiding

|  | CO Conversion (%) | CH$_4$ Selectivity (%) |
|---|---|---|
| Presulfiding Conditions |  |  |
| Presulfided at 500° C. with N$_2$, H$_2$ and DMDS (Base Case) | 85 | 52 |
| Presulfiding Temperature |  |  |
| 500° C. | 85 | 52 |
| 480° C. | 83 | 52 |
| 450° C. | 82 | 52 |
| Presulfiding Medium |  |  |
| N$_2$, H$_2$ with DMDS | 85 | 52 |
| H$_2$ with DMDS | 79 | 52 |
| N$_2$, H$_2$ with H$_2$S | 81 | 52 |
| H$_2$ with H$_2$S | 85 | 52 |

Effect of Presulfiding Medium: The MoS$_2$ catalyst was evaluated for different presulfiding media: hydrogen sulfide, a gaseous medium, and dimethyl disulfide, a liquid sulfiding medium in the presence of gases such as N$_2$ and H$_2$. Molybdenum trisulfide can be converted to disulfide either by reduction with hydrogen or thermal decomposition in N$_2$. A number of experiments were done to reduce and presulfide the MoS$_2$ catalyst with the two different sulfiding agents, as shown in Table 2. No major differences in MoS$_2$ activity for methanation were observed for different presulfiding media.

Figure 8:
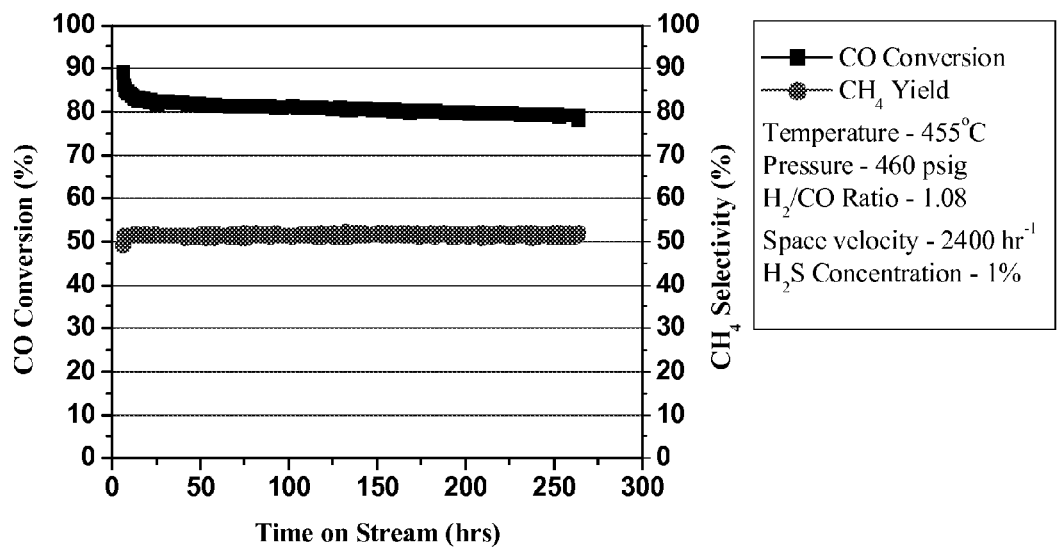
FIG. 8: (A) CO conversion and methane yield for sulfur-tolerant MoS2 catalyst in the presence of 2200 ppm H2S obtained from the thermal decomposition of dimethyl disulfide (DMDS). (B) CO conversion and methane selectivity for sulfur-tolerant MoS2 catalyst in the presence of 1% H2S obtained directly from a gas cylinder of 5% H2S in hydrogen.
Figure 8:
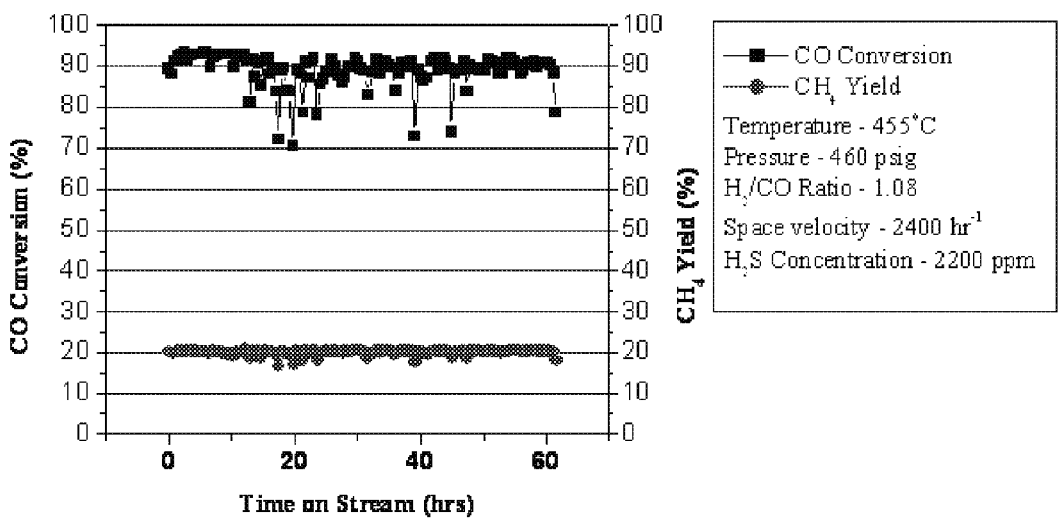

Results:

A 2.5 day run was conducted on the MoS$_2$ catalyst with 2200 ppm H$_2$S obtained from thermal decomposition of dimethyl disulfide (DMDS). A plot of CO conversion is shown in FIG. 8(a). The catalyst resultant in 95% conversion, but due to the low flow of the DMDS syringe pump, there were some scattering in the data. In order to obtain stable data without the disturbances, a gas cylinder of 5% H$_2$S in H$_2$ was bought and an 11-day experiment was conducted with feed gases containing 1% H$_2$S. The result was stable after some initial deactivation as shown in FIG. 8(b). The CO conversion obtained was around 80%. It was higher than previous CO conversion of 76% (Meyer, 1982) for 1% H$_2$S. The catalyst was evaluated with feed gases simulating raw gasifier effluents for extended periods to measure the effects of CO$_2$, H$_2$O, benzene, phenol, ammonia, and higher hydrocarbons, etc.

Effect of Process Conditions: The effects of various parameters such as H$_2$S in the synthesis gas, space velocity, temperature and pressure on the activity and stability of the catalyst influence catalyst selection and design of the process.

Figure 9:
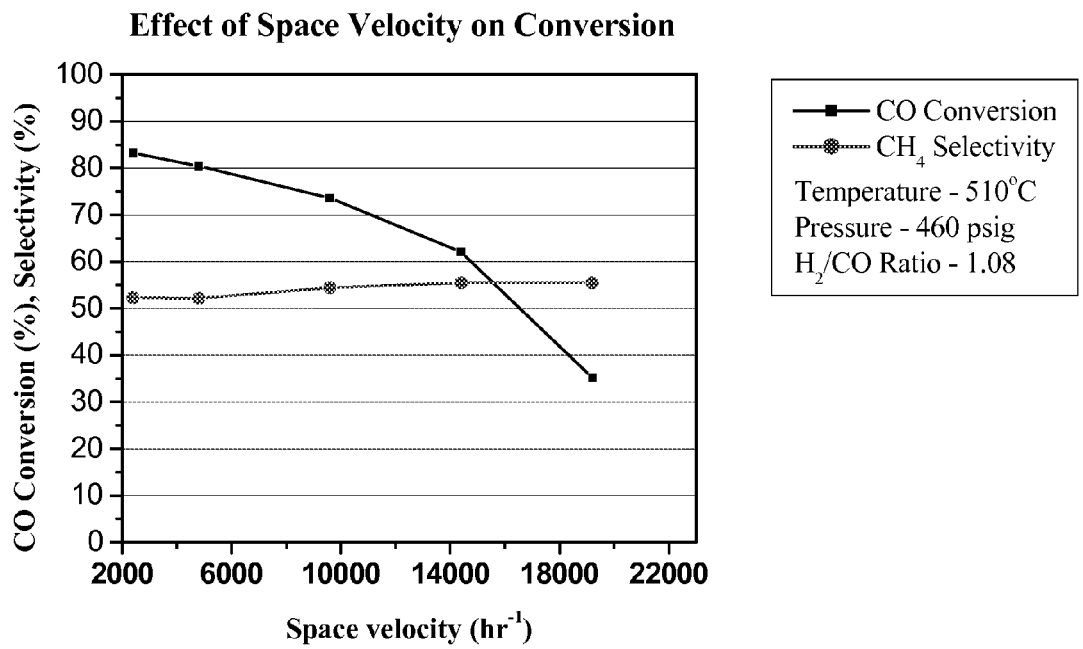
FIG. 9: CO conversion and methane selectivity for sulfur-tolerant MoS2 catalyst as a function of space velocity during the production of substitute natural gas from synthesis gas.

Effect of Space Velocity: The effect of GHSV on CO conversion and methane selectivity for the MoS$_2$ catalyst is presented in FIG. 9. As expected, increases in GHSV decrease CO conversion and this decrease was not linear. The CH4 selectivity was fairly constant over the entire range of space velocity examined (2000 hr$^{-1}$ to 20,000 hr$^{-1}$). Since the methanation reaction is so exothermic, the space velocity should be chosen so that there is just enough conversion to keep the temperature within the acceptable limits.

Figure 10:
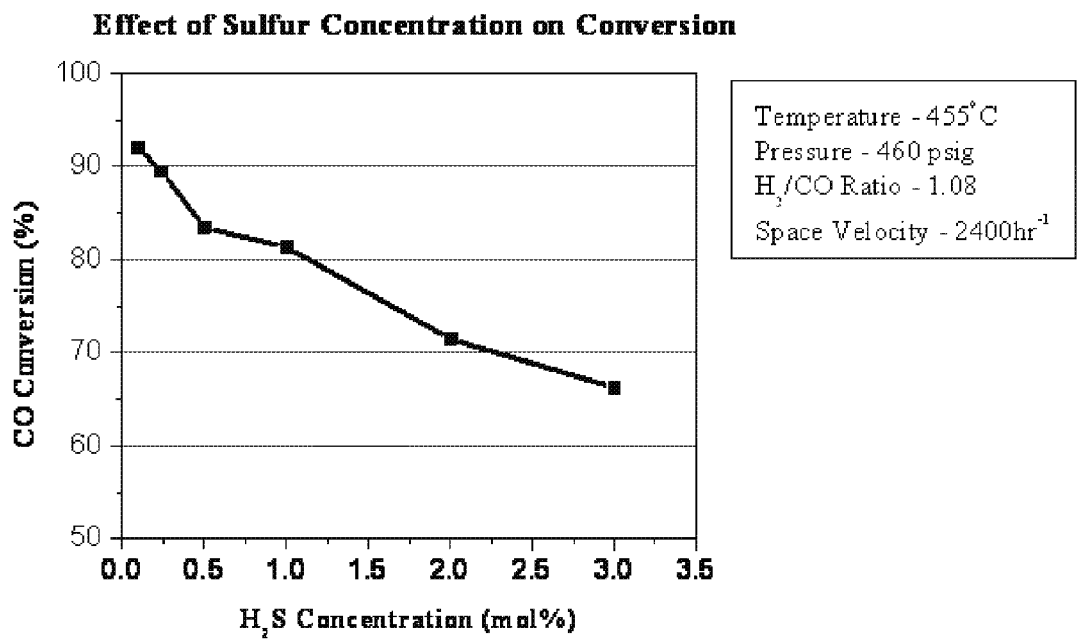
FIG. 10: CO conversion for sulfur-tolerant MoS2 catalyst as a function of H2S concentration in the feed gas for the production of substitute natural gas from synthesis gas.
Figure 11:
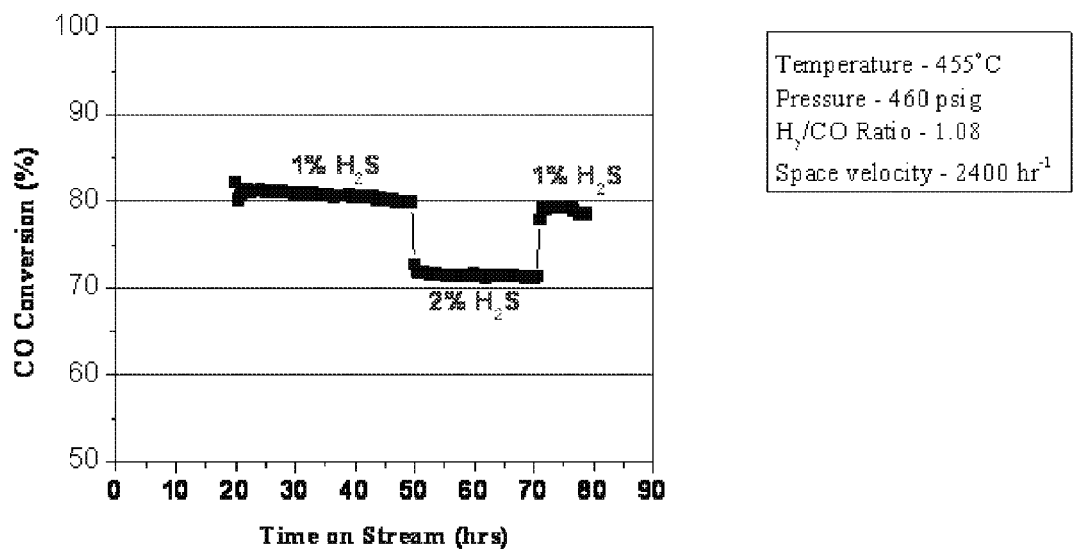
FIG. 11: CO conversion for sulfur-tolerant MoS2 catalyst as a function of H2S concentration in the feed gas.

Effect of H$_2$S in Synthesis Gas: The effect of H$_2$S in the feed gas on CO conversion was measured and is given in FIG. 10. As shown in FIG. 10, there is a sharp decrease in CO conversion with increasing H$_2$S concentration. However MoS$_2$ is a sulfur-tolerant catalyst and so the effect of H$_2$S on this catalyst is reversible. FIG. 11 shows that when H$_2$S concentration was increased from 1% to 2% of the feed gas, the CO conversion reduced from 80% to 71%. But when the H$_2$S level was reduced back to 1%, the CO conversion returned to 80%. These data show that for MoS$_2$ catalysts, H$_2$S is more like an inhibitor than a poison. On the other hand, H$_2$S acts as a poison for the nickel catalyst because the reduction in the activity is not reversible.

Figure 12:
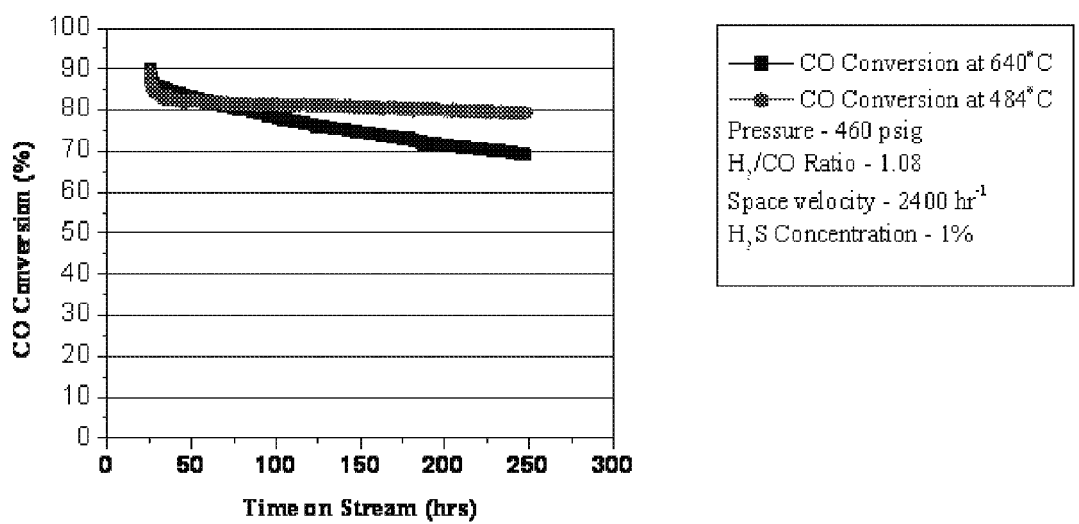
FIG. 12: CO conversion for sulfur-tolerant MoS2 catalyst as a function of temperature during the production of substitute natural gas from synthesis gas.

Effect of Temperature: In order to check the upper temperature limit of the MoS$_2$ catalyst, catalysts were evaluated at temperatures higher than 455° C. FIG. 12 shows the CO conversion for two furnace set point temperatures of 455° C. and 600° C. over a period of 11 days. These furnace set point temperatures corresponded to catalyst bed temperatures of 484 and 640° C. (~1180° F.), respectively. It is clear from the plot that initial conversion is 90% at a catalyst temperature of 640° C. compared to 89% at 484° C. But the decline in activity is much faster at the higher temperature. The deactivation rate from the last two days of data from 11-day experiment is 0.009% loss in CO conversion per hr for 484° C. (~900° F.) and 0.045% loss in CO conversion per hr for 640° C. The higher deactivation rate at the higher temperature is due to more sintering. A deactivation study longer than 11 days would be required to see if the catalyst finally stabilizes at higher temperatures.

Example 6: Co-Precipitation in Acid

The MoS$_2$, catalyst along with zirconium as promoter was prepared by co-precipitation using nitric acid. 32 grams of ammonium tetrathiomolybdate was dissolved in 492 mL of distilled water. 14.2 grams of zirconyl hydrate nitrate dissolved in 30.2 grams of DI water was added to this solution. The solution was acidified with 0.1 M dilute nitric acid at pH 5 to precipitate the MoS$_2$ catalyst. The precipitate was then filtered, washed first with distilled water and then acetone. Then 40 grams of elemental sulfur stirred in acetone was added to the filtered cake. The resultant cake was dried in an oven under N$_2$ atmosphere at 80° C. for 4 hrs. The dried mixture is collected, weighed, palletized and prepared for presulfiding and reduction for further evaluation.

To evaluate the catalyst activity, 15 g of MoS$_2$ catalyst were loaded into a ½ inch stainless steel reactor and pre-sulfided by rapidly heating the reactor to 450° C. at 460 psig with N$_2$ flowing at a rate of 187.5 cc/min along with DMDS flow at 0.4 ml/hr. When the temperature reached 450° C., the nitrogen gas flow was switched to a stream of hydrogen along with DMDS flow at 0.59 mL/hr. The reactor was kept at 500° C. under H$_2$ and DMDS for 5 hours. After 5 hours, the reactor was cooled by passing a stream of N$_2$ through the reactor and used for further evaluation. For the activity test, sorbitol was selected as C6 sugar alcohol. Diesel was co-fed to the reactor as diluent.

The detailed reaction conditions and catalyst performance are listed in Table 3, below. It is clearly shown that the catalyst is active for sorbitol hydrogenation to hydrocarbons. The sorbitol conversion was about 81% at 250° C. (~480° F.). With the increase in reaction temperature to 315° C. (~600° F.), the sorbitol conversion was increased to ~95%. At 280° C. (~535° F.) the sorbitol conversion was approximately 91%. C6 hydrocarbons, such as hexanes, are the main products produces from sorbitol conversion.

TABLE 3

Sorbitol Conversion to C6 hydrocarbons at varying temperatures

| Run# | 250° C. | 280° C. | 315° C. |
|---|---|---|---|
| Temp, C. | 250 | 280 | 315 |
| Pressure, Psig | 1200 | 1200 | 1200 |
| 70% sorbitol rate, ml/min | 6 | 6 | 6 |
| Diesel rate, ml/min | 12 | 12 | 12 |
| $H_2$ rate, ml/min | 200 | 200 | 200 |
| Sorbitol conversion, % | 81.0 | 91.2 | 95.0 |
| C6 hydrocarbons in collected liquid product, wt % | 10.6 | 19.0 | 19.7 |

In conclusion, CO conversion was increased from 75% to 85% (455° C., 460 psig, GHSV=2400 hr$^{-1}$, $H_2S$=1% (mol), $H_2$/CO=1.08) by using a zirconium promoter composition during co-precipitation of a high surface area $MoS_2$ catalyst at the appropriate pH. Elemental sulfur powder is important for the stability of the $MoS_2$ catalyst. Addition of promoters such as nickel, magnesium, potassium, palladium, alumina, silica and titania did not result in any improvements in the methanation activity. High surface area $MoS_2$ catalyst is resultant from fast reduction of molybdenum trisulfide in hydrogen into the active molybdenum disulfide form. The choice of presulfiding agent, dimethyl disulfide or hydrogen sulfide, did not result in differences in methanation activity. Presence of high levels of hydrogen sulfide reduces the methanation activity of the $MoS_2$ catalyst but activity returns when the hydrogen sulfide level drops. Molybdenum catalyst was tested at 640° C. and it retained activity although deactivation rate was 0.045% compared to 0.009% loss in CO conversion per hour at 484° C. Despite substantial improvement, molybdenum catalysts are less active than nickel catalysts for methanation. However, very high activity is not required because of high heat generation in methanation which places practical limits on per-pass conversion. Thus the novel sulfur tolerant MoS2 catalyst provides a catalyst that is active at higher temperatures allowing unique Methanation process design and implementation due to unique catalytic properties.

REFERENCES

All of the references cited herein are expressly incorporated by reference. The discussion of any reference is not an admission that it is prior art to the present invention, especially any reference that may have a publication data after the priority date of this application. Incorporated references are listed again here for convenience:

1. U.S. Pat. No. 3,904,386, "Combined shift and methanation reaction process for the gasification of carbonaceous materials." Grabosk and Donath, U.S. Dept. Interior, (1975).
2. U.S. Pat. No. 4,151,191, "Sulfur resistant molybdenum catalysts for methanation." Happel and Hnatow, American Gas Assoc., (1979).
3. U.S. Pat. No. 4,491,639, EP0107358, "High activity transition metal catalysts." Happel, et al., Gas Research Inst. (1984).
4. U.S. Pat. No. 4,867,840, U.S. Pat. No. 5,026,473, "Method of making artificially textured layered catalyst," Roxlo, Exxon Chem. Eng. Res. (1989).
5. U.S. Pat. No. 4,962,077, "Transition metal tris-dithiolene and related complexes as precursors to active catalysts," Halbert, et al., Exxon Res. Eng. Co., (1990).
6. U.S. Pat. No. 5,162,281, "Method of preparing hydrotreating catalyst for hydrocarbon oil," Kamo & Kanai, Sumitomo Metal Mining Co. Ltd. (1992).
7. U.S. Pat. No. 6,156,693, U.S. Pat. No. 6,451,729, "Method for preparing a highly active, unsupported high surface-area $MoS_2$ catalyst," Song, Penn. State (2002).
8. U.S. Pat. No. 6,559,092, "Precarbonisation of a hydrotreatment catalyst," Dufresne, et al., Europeenne de Retraitement de Catalyseurs Eurecat (2003).
9. U.S. Pat. No. 7,223,713, US2005059545, US2007238607, WO2005023416 "Molybdenum sulfide/carbide catalysts," Alonso, Univ. Texas (2007).
10. U.S. Pat. No. 7,361,624, US2003173256, WO03000410, "Catalyst for hydrogenation treatment of gas oil and method for preparation thereof, and process for hydrogenation treatment of gas oil," Fujikawa, et al., Cosmo Oil Co Ltd. (2003).
11. U.S. Pat. No. 7,361,624, "Catalyst for hydrotreating gas oil, process for producing the same, and method for hydrotreating gas oil," Assignee: Cosmo Oil Co., Inventors: Fujikawa, et al. (2008).
12. U.S. Pat. No. 7,435,760, US2005267224, US2009007996, WO2006076023, "Method of generating hydrocarbon reagents from diesel, natural gas and other logistical fuels," Herling, et al., Battelle Memorial Inst. (2008).
13. EP0120590 "Pipeline gas from sulfur containing raw or synthesis gas." Happel, et al., Gas Research Inst. (1984).
14. U.S. Ser. No. 12/849,109, "Hydrotreating Carbohydrates," ConocoPhillips Co., Sughrue, et al., (2010).
15. US 2010-0099933, "Integrated Process For Converting Carbohydrates To Hydrocarbons," ConocoPhillips Co., Yao, et al., (2010).
16. U.S. Ser. No. 12/912,164, "Conversion Of Carbohydrates To Hydrocarbons," ConocoPhillips Co., Yao, et al., (2010).
17. U.S. Ser. No. 61/424,896, "Production Of Renewable Fuels," ConocoPhillips Co., Bares, et al., (2010).
18. Reid, "Early development of SNG [substitute natural gas] processes." Pap. Substitute Nat. Gas Hydrocarbon Liq., SNG Symp., 1:81-113 (1973).
19. White, et al., "RMProcess." Adv. Chem. Ser., Methanation Synth. Gas, Symp. 146:138-48 (1975).
20. White, et al, "The RMProcess." Energy Commun., 2:45-63 (1976).
21. Koch, et al., "Application of Conoco's Super-Meth combined shift/methanation process to the BGC/Lurgi slagging gasifier." Coal Technol. (Houston) 2:51-80 (1979).
22. Happel, et al., "Direct catalytic methanation of raw synthesis gas." Proc. Int. Gas Res. Conf., 1:723-9 (1980).
23. Dissinger, et al., "Dynamic simulation of methanation reactors, interstage heat exchangers, and controllers." Chem. Eng. Commun., 4:577-91 (1980).
24. Sudbury, et al., "Conoco's capabilities in methanation of coal derived syngases." Proc. Int. Gas Res. Conf., 1:687-701 (1980).
25. Happel, et al., "Methanation with nonmetallic catalysts." Chem. Ind. (Dekker), 5:235-47 (1981).
26. Happel, J., et al., "Direct methanation of raw synthesis gas." Proc. Int. Gas Res. Conf., 2:275-80 (1982).
27. Happel, J., et al., "Methanation kinetics with transition element catalysts." Proc. Int. Gas Res. Conf., 493-500 (1983).
28. Happel, J., et al., "Methanation with transition element catalysts." Proc. Int. Gas Res. Conf., 406-14 (1985).

29. Mitchell, "Computer modelling of a molybdenum disulfate catalyst: density functional calculations on molybdenumsulfur clusters," C. Plant. Proc. Vth Workshop Hydrotreating Catalysts: Bul. Soc. Chim. Belg., 104, 293 (1995).
30. Lukes and Wallach, "The Great Plains Synfuels Plant—An evolution." Proc.—Annu Int. Pittsburgh Coal Conf., 20:23-43 (2003).
31. Barrera, "Dibenzothiophene Hydrodesulfurization Activity of $MoS_2$ Supported in Sol-Gel $ZrO_2$—$TiO_2$ Mixed Oxides," Petroleum Science and Technology, 22:87-101 (2004).
32. Torrisi, et al., "Catalyst Advancements to Increase Reliability and Value of ULSD Assets," National Petrochemical & Refiners Assoc., Annual Meeting (2005).
33. Udengaard, et al., "High temperature methanation process-revisited." Proc.—Annu Int. Pittsburgh Coal Conf., 23:2 5/1-2 5/5 (2006).
34. Bohnet, "Cleaner Fuel by Nanoparticles," Siemens, Innovation Report (2007). www.innovations-report.com/html/reports/environment sciences/report-78262.html
35. Walston and R.T.G. III, "Coal-derived syngas to substitute natural gas: Technology alternatives and economic implications (2007).
36. Anand, et al., "Great Plains Coal to Substitute Natural Gas (SNG) Plant." (2007).
37. Huang, Z., X. Wang, and Y. Fu, Methanation activity of sulfided molybdenum catalysts supported on mixed carrier. Ranliao Huaxue Xuebao, 1990. 18(2): p. 123-9.
38. Lee, A. L., Evaluation of coal conversion catalysts. Final report January 1978-December 1985. 1987, Inst. Gas Technol., Chicago, Ill., USA. p. 82 pp.
39. Happel, J. and M. A. Hnatow, Process for making High activity transition metal catalysts. 1982, (Gas Research Institute, USA). US. p. 9 pp.
40. Nahas, N. C., Exxon catalytic coal gasification process. Fundamentals to flowsheets. Fuel, 1983. 62(2): p. 239-41.
41. Nahas, N. C., Catalytic gasification of petroleum residues to methane. 2003, (Petro 2020, LLC, USA). Application: US. p. 8 pp.
42. Nahas, N. C., Catalytic methane synthesis can extend hydrocarbon supply. Oil Gas J., 2004. 102(37): p. 18-20, 22,24.
43. Nahas, N. C. and J. E. Gallagher, Jr., Catalytic gasification predevelopment research. Proc.—Intersoc. Energy Conyers. Eng. Conf., 1978. 13(3): p. 2143-7.
44. Nahas, N. C. and C. J. Vadovic, Catalytic gasification of coal. 1978, (Exxon Research and Engineering Co., USA). Application: US. p. 6 pp.
45. Anand, M., Catalytic Steam Gasification of Coal for the Production of Substitute Natural Gas (SNG). 2008: Bartlesville.
46. Meyer, H. S., et al., Direct methanation—a new method of converting synthesis gas to substitute natural gas. Prepr. Pap.—Am. Chem. Soc., Div. Fuel Chem., 1982. 27(1): p. 109-15.
47. Cover. A. E., et al., Advanced Coal Gasification Technical Analysis, Final report (April 1985-December 1988), in GRI-89/0004. 1989.
48. Smelser. S. C., et al., Evaluation of Advanced Gas Processing Concepts For Fluidized Bed Gasification in GRI-87/0158. November 1985-December 1987. p. 90 pp

The invention claimed is:

1. A substitute natural gas production system comprising:
A gasifier unit,
an oil quench unit,
a water quench and ammonia recovery unit,
a methanation unit that comprises a methanation catalyst, a CO2 and water removal unit, and a sulfur removal unit,
wherein said methanation catalyst comprises molybdenum disulfide (MoS2), zirconium, (Zr) and elemental sulfur,
wherein said methanation catalyst is formed by co-precipitation in the presence of Zr at a pH of greater than 3.0,
wherein said methanation catalyst further comprises a promoter that is selected from the group consisting of $MgNO_3$, $PdNO_3$ and combinations thereof.

2. The system of claim 1, wherein said methanation catalyst is pre-sulfided at between about 450° C. and about 500° C. in the presence of one or more members of the group consisting of $N_2$, $H_2$, DMDS and $H_2S$.

3. The system of claim 1, wherein said methanation catalyst contains a ratio of Zr/Mo between about 0.6 and about 0.8.

* * * * *